US008846413B2

(12) United States Patent (10) Patent No.: US 8,846,413 B2
Ruzicka (45) Date of Patent: Sep. 30, 2014

(54) METHOD FOR DETERMINING THE CONCENTRATION OF THE ADIPOCYTIC FORM OF THE FATTY ACID BINDING PROTEIN (A-FABP, FABP4, P2)

(75) Inventor: Viktor Ruzicka, Brno (CZ)

(73) Assignee: Biovendor Laboratory Medicine, Inc., Brno (CZ)

( * ) Notice: Subject to any disclaimer, the term of this patent is extended or adjusted under 35 U.S.C. 154(b) by 1310 days.

(21) Appl. No.: 11/988,822

(22) PCT Filed: Jul. 21, 2006

(86) PCT No.: PCT/IB2006/002383
§ 371 (c)(1),
(2), (4) Date: Mar. 3, 2009

(87) PCT Pub. No.: WO2007/063363
PCT Pub. Date: Jun. 7, 2007

(65) Prior Publication Data
US 2009/0181886 A1 Jul. 16, 2009

(30) Foreign Application Priority Data

Jul. 21, 2005 (DE) .......................... 10 2005 034 788

(51) Int. Cl.
*G01N 33/543* (2006.01)
*G01N 33/92* (2006.01)
(52) U.S. Cl.
CPC .......... *G01N 33/92* (2013.01); *G01N 2800/042* (2013.01); *G01N 2800/044* (2013.01); *Y10S 436/811* (2013.01)
USPC ........... 436/518; 435/7.1; 435/7.92; 436/501; 436/811
(58) Field of Classification Search
None
See application file for complete search history.

(56) References Cited

U.S. PATENT DOCUMENTS

2007/0042425 A1* 2/2007 Hochstrasser et al. ......... 435/7.1

FOREIGN PATENT DOCUMENTS

GB WO 2005/029088 * 3/2005 ............. G01N 33/68

OTHER PUBLICATIONS

Strongin, Laboratory Diagnosis of Viral Infections, Sensitivity, Specificity, and Predictive Value of Diagnostic Tests: Definitions and Clinical applications, Lennette, ed. Marcel Dekker, Inc. New York, pp. 211-219, 1992.*
Yun et al., Association between adipocyte fatty acid-binding protein levels and childhood obesity in Korean childrean, Metaboism Clinical and Experimental 58, 2009, pp. 798-802.*
Biovender Research and Diagnostic Products, Human Adipocyte FABP ELISA (Human FABP4 ELISA), Cat. No. RD191036200R, Aug. 2012, pp. 1-24.*

Xu et al., "Adipocyte Fatty Acid—Binding Protein Is a Plasma Biomarker Closely Associated with Obesity and Metabolic Syndrome", Clinical Chemistry, Mar. 2006, vol. 52, No. 3, pp. 405-413.
Xu et al., "Circulating Adipocyte—Fatty Acid Binding Protein Levels Predict the Development of the Metabolic Syndrome: A 5-Year Prospective Study", Circulation, Mar. 27, 2007, vol. 115, No. 12, pp. 1537-1543.
Coll et al., "The Fatty Acid Binding Protein-4 (FABP4) is a Strong Biomarker of Metabolic Syndrome and Lipodystrophy in HIV-infected Patients", Atherosclerosis, Jul. 2008, vol. 199, Issue 1 , pp. 147-153.
Cabre et al., "Fatty Acid Binding Protein 4 is Increased in Metabolic Syndrome and with Thiazolidinedione Treatment in Diabetic Patients", Atherosclerosis, Nov. 2007, vol. 195, No. 1, e150-e158.
Park et al., "The Role of Serum Adipocyte Fatty Acid-Binding Protein on the Development of Metabolic Syndrome is Independent of Pro-Inflammatory Cytokines", Nutr. Metab. Cardiovasc. Dis., Jun. 2012, vol. 22, No. 6, pp. 525-532.
Hsu et al., "Fasting Serum Level of Fatty-Acid-Binding Protein 4 Positively Correlates with Metabolic Syndrome in Patients with Coronary Artery Disease", Circ J., Feb. 2010, vol. 74, No. 2, pp. 327-331.
Choi et al., Serum Adipocyte Fatty Acid-Binding Protein, Retinol-Binding Protein 4, and Adiponectin Concentrations in Relation to the Development of the Metabolic Syndrome in Korean Boys: a 3-y Prospective Cohort Study1-5, Am J Clin Nutr, Jan. 2011, vol. 93, No. 1, pp. 19-26.
Tsai et al., "Fasting Serum Fatty Acid-Binding Protein 4 Level Positively Correlates with Metabolic Syndrome in Hemodialysis Patients", Archives of Medical Research, Oct. 2010, vol. 41, Issue 7 , pp. 536-540.
Terra et al., "FABP 4 is Associated with Inflammatory Markers and Metabolic Syndrome in Morbidly Obese Women", Eur J Endocrinol., Apr. 2011, vol. 164, No. 4, pp. 539-547.
Human Adipocyte FABP ELISA (Human FABP4 ELISA), BioVendor Research and Diagnostic Products, Product Data Sheet, pp. 1-28, Version 99 050112 19, BioVendor, Candler, NC, 1999.
Abdelnaby, Khalyfa, Fatty-acid binding protein 4 gene variants and childhood obesity: potential implications for insulin sensitivity and CRP levels, Lipids in Health and Disease, Sep. 18, 2010, pp. 1-6, BioMed Central.
Bhushan, Bharat, PhD., Fatty-Acid Binding Protein 4 Gene Polymorphisms and Plasma Levels in Children with Obstructive Sleep Apnea, NIH Public Access Author Manuscript, Aug. 2011, pp. 1-15.
Lazaro, I., Fatty Acid-Binding Protein-4 Plasma Levels Are Associated to Metabolic Abnormalities and Response to Therapy in Girls and Young Women and Androgen Excess, Gynecol Endocrinol, EPub Nov. 2011, p. D13, Reus Spain.
Roshanak Bagheri, MD, Relation of Plasma Fatty Acid Binding Proteins 4 and 5 With the Metabolic Syndrome, Inflammation and Coronary Calcium in Patients With Type-2 Diabetes Mellitus, NIH Public Access Author Manuscript, Oct. 2010, pp. 1-13.

(Continued)

*Primary Examiner* — Gary W Counts
(74) *Attorney, Agent, or Firm* — Buchanan Ingersoll & Rooney PC

(57) ABSTRACT

Products and methods for the research, diagnosis, risk assessment, course monitoring, treatment and prophylaxis of various metabolic disorders and their early forms, concomitant diseases and secondary diseases are provided. Metabolic diseases include, for example, metabolic syndrome, non-insulin-dependent diabetes, (type II diabetes), insulin resistance, obesity (adiposis), in addition to diseases that are associated with disorders of the fatty acid metabolism. Methods may include analysis of the concentration of the adipocytic form of the fatty acid binding protein (A-FABP, FABP 4, P2) in various bodily fluids.

10 Claims, 25 Drawing Sheets

(56) References Cited

OTHER PUBLICATIONS

Krzystek-Korpacka, M., Circulating Adipocyte Fatty Acid-Binding Protein, Juvenile Obesity, and Metabolic Syndrome, J. Pediatr Endocrinol Metab., 2011, p. D16, Wroclaw, Poland.

Aeberli, I., The Increase of Fatty Acid-Binding Protein aP2 in Overweight and Obese Children: Interactions With Dietary Fat and Impact on Measures of Subclinical Inflammation, Human Nutrition Laboratory, Institute of Food Science and Nutrition, Oct. 2008, p. D18, Zurich, Switzerland.

* cited by examiner

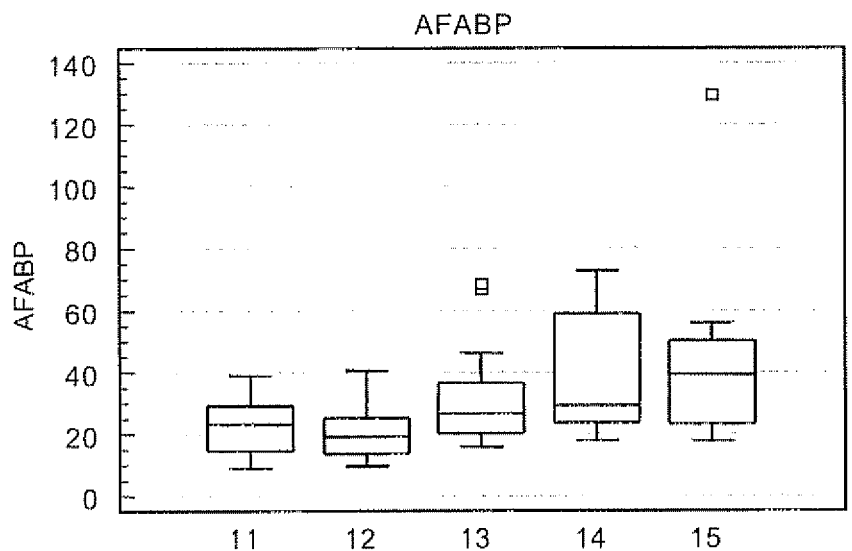

11= healthy, 12=dyslipidaemia, 13= DM, 14=obesity, 15= met. syndrom

Fig. 1: Determination of A-FABP in the serum of 486 volunteers (100 standard-weight, healthy volunteers, 100 patients with dyslipidaemia without obesity and without further features of the metabolic syndrome, 86 type II diabetics, 100 obese und 100 patients with metabolic syndrome.

In the groups of volunteers in question, the A-FABP concentration ranges shown were found (values on the Y axis are ng/ml):

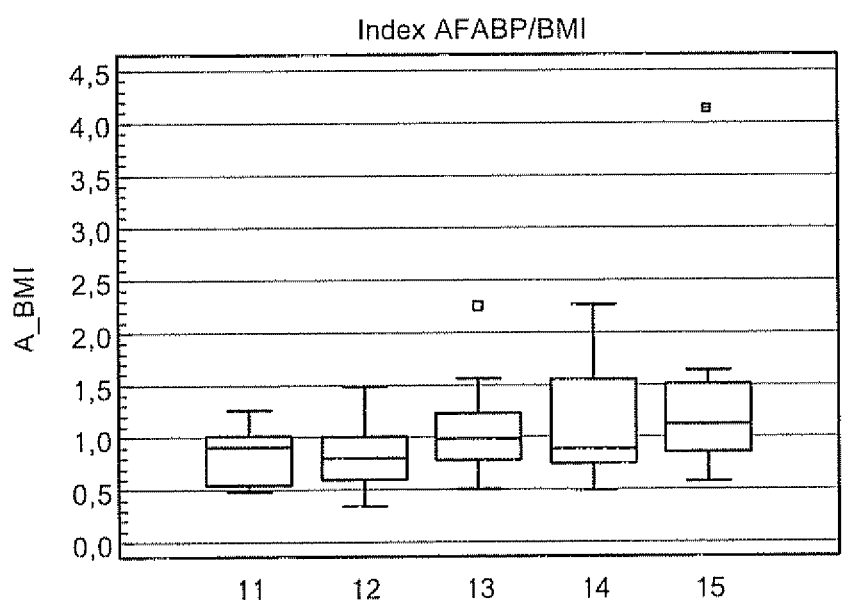
Fig. 2: Correction of the values from Fig. 1 to the Body Mass Index (A-FABP divided by BMI = A_BMI) resulted in the distributions as shown in Figure 2.

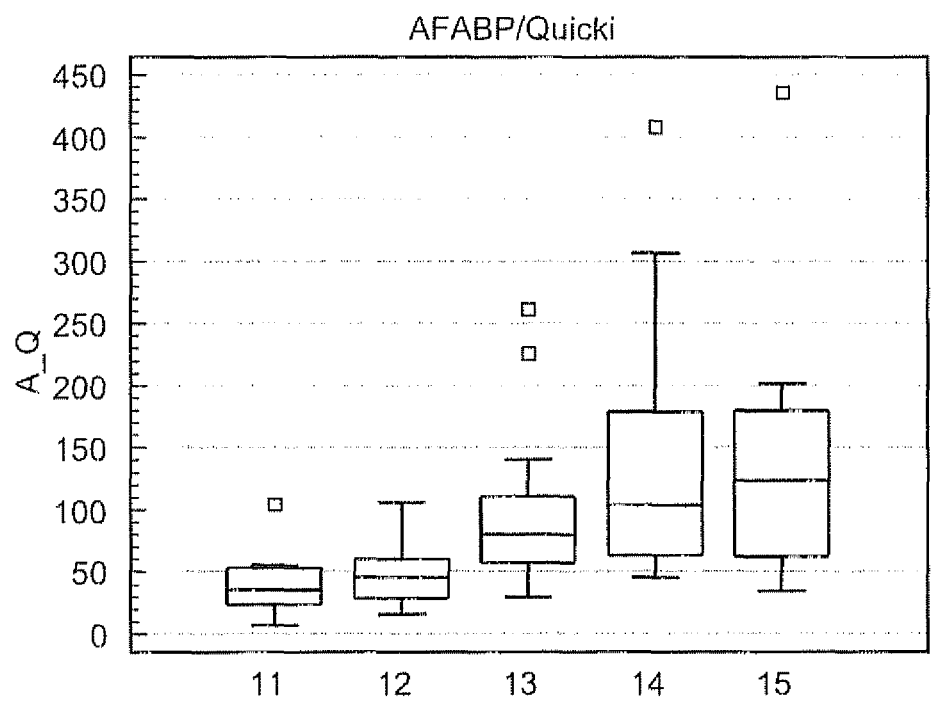
Fig. 3: A-FABP values divided by the values of the QUICKI Index

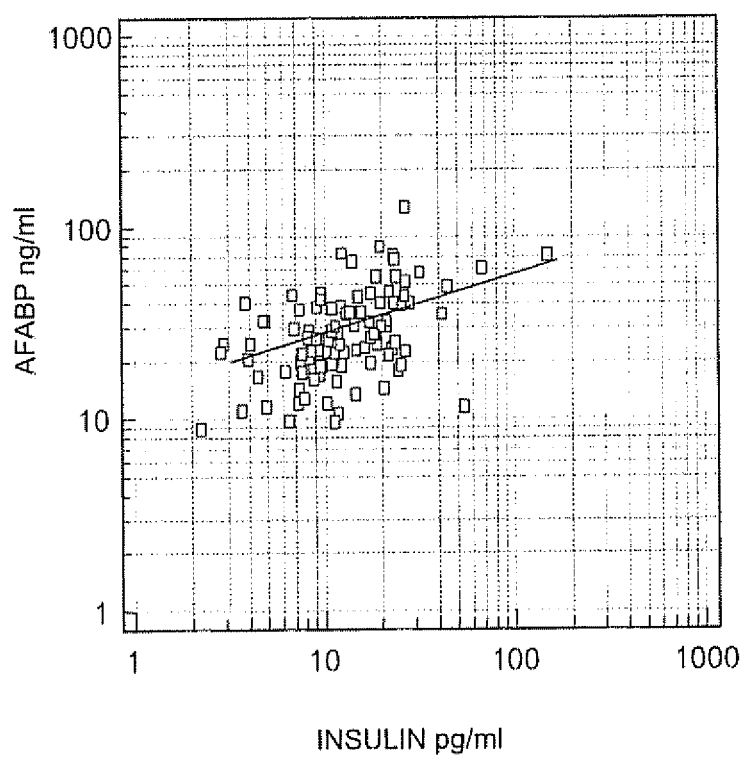
Fig. 4: Correlation between measured concentrations of A-FABP and insulin of volunteers.

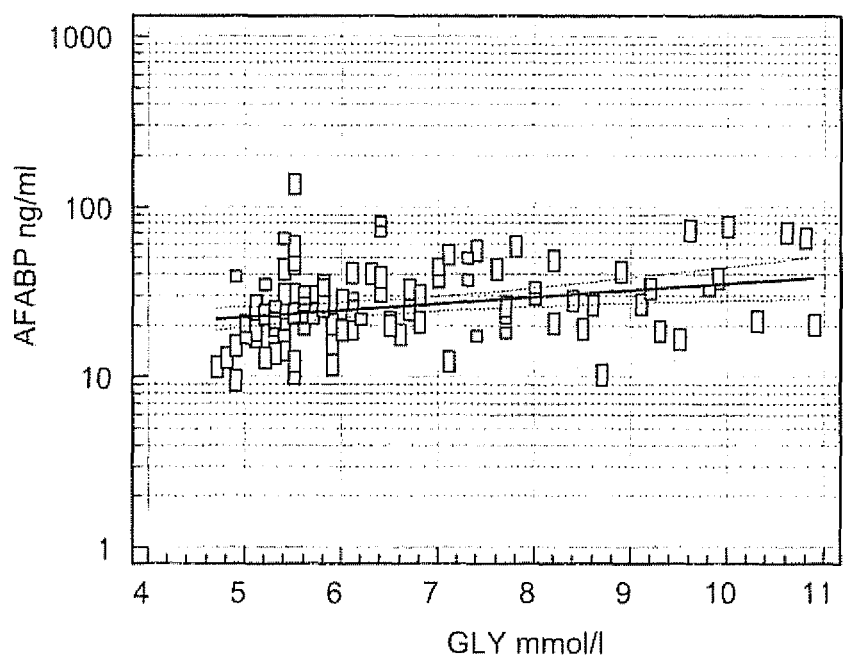
Fig. 5: Correlation between measured concentrations of A-FABP and glucose of volunteers.

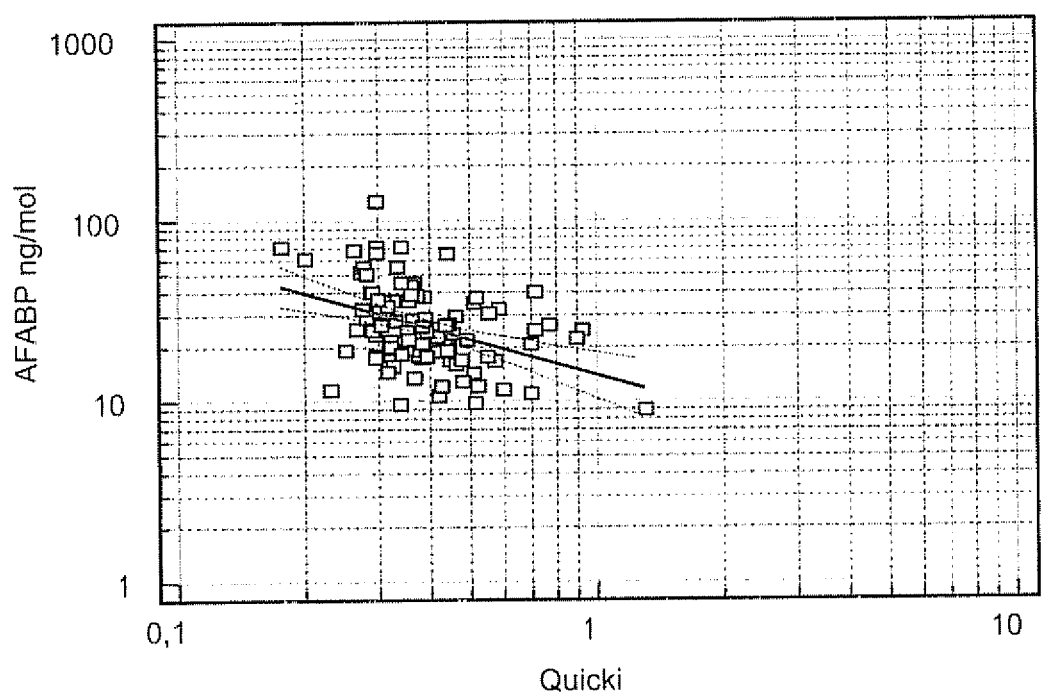
Fig. 6: Correlation between measured concentrations of A-FABP and QUICKI Index.

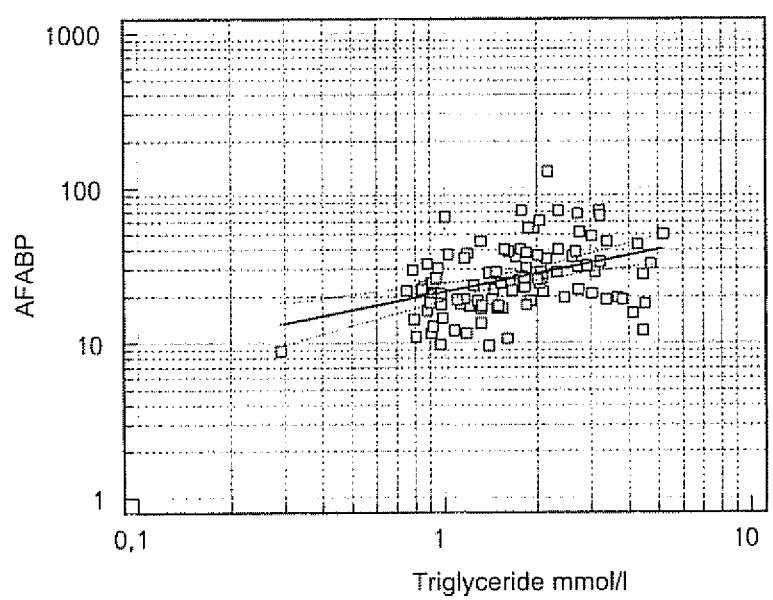
Fig. 7: Correlation between measured concentrations of A-FABP and triglycerides

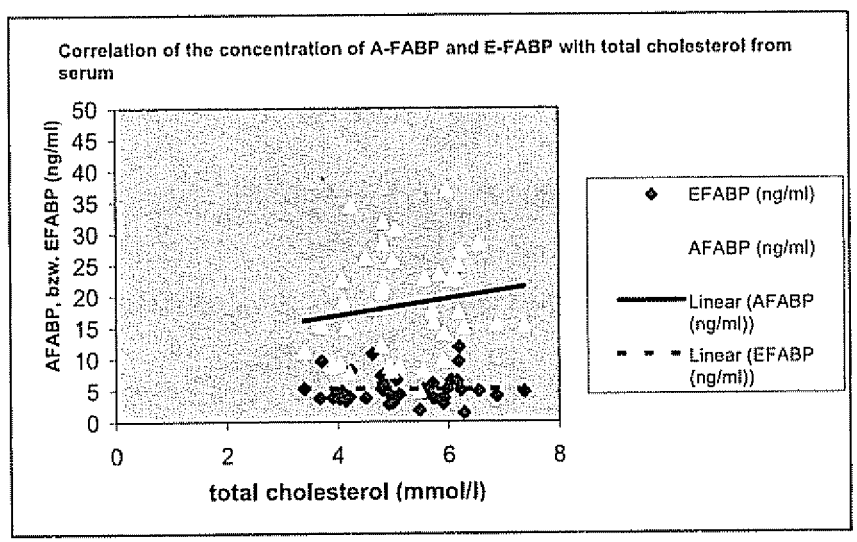
Fig. 8: Correlation of the concentration of A-FABP and E-FABP with total cholesterol from serum (examination of samples from 48 women).

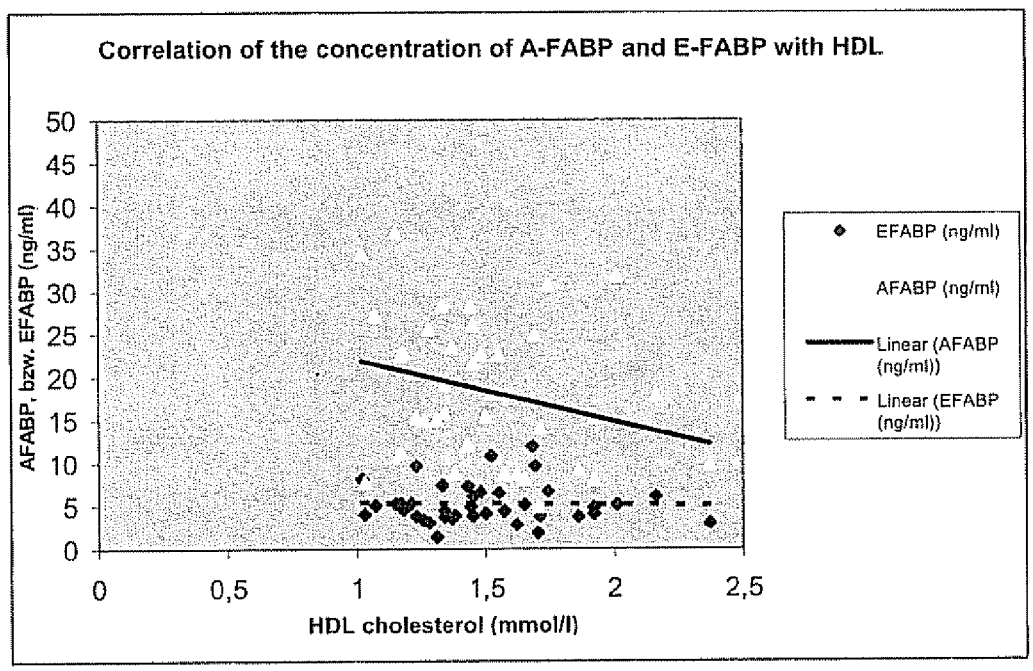
Fig. 9: Correlation of the concentration of A-FABP and E-FABP with HDL cholesterol from serum (examination of samples from 48 women).

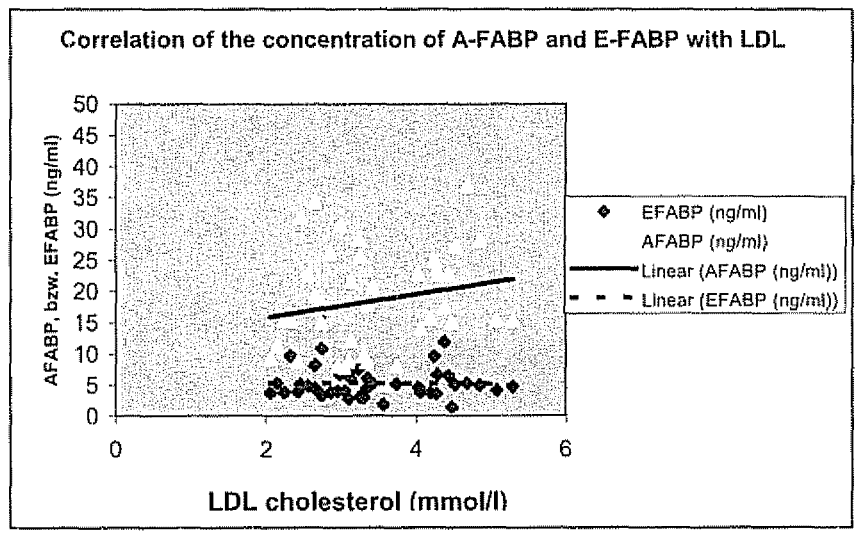
Fig. 10: Correlation of the concentration of A-FABP and E-FABP with LDL cholesterol from serum (examination of samples from 48 women).

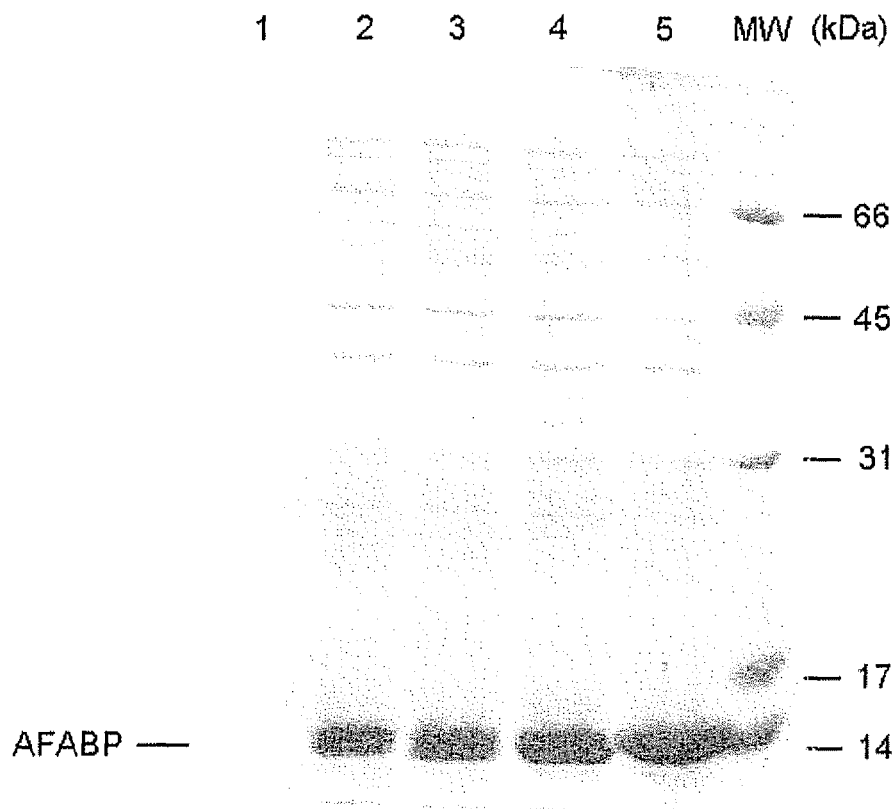
Fig. 11: Electrophoretic separation by SDS PAGE of cell lysates and visualisation of the protein bands received by Coomassie dyeing.
Description of the tracks
1. $T_0$, i.e. at the moment of addition of IPTG
2. $T_2$, i.e. 2 hours after addition of IPTG
3. $T_4$, i.e. after 4 hours at the end of the expression
4. Supernatant after ultrasound treatment of the bacteria
5. Inclusion corpuscles

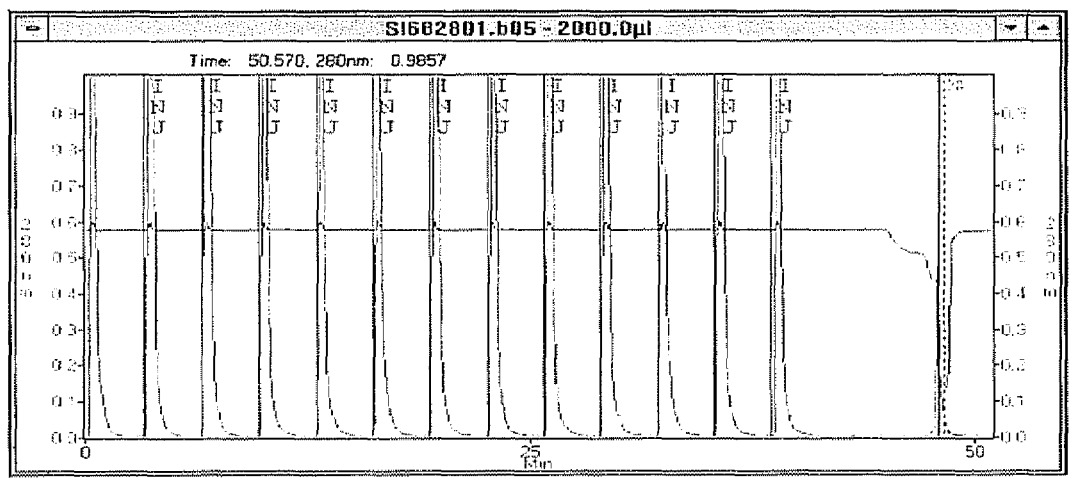
Fig. 12: Result of the affinity chromatography of anti-A-FABP antibodies from rabbits from a column with bound A-FABP.

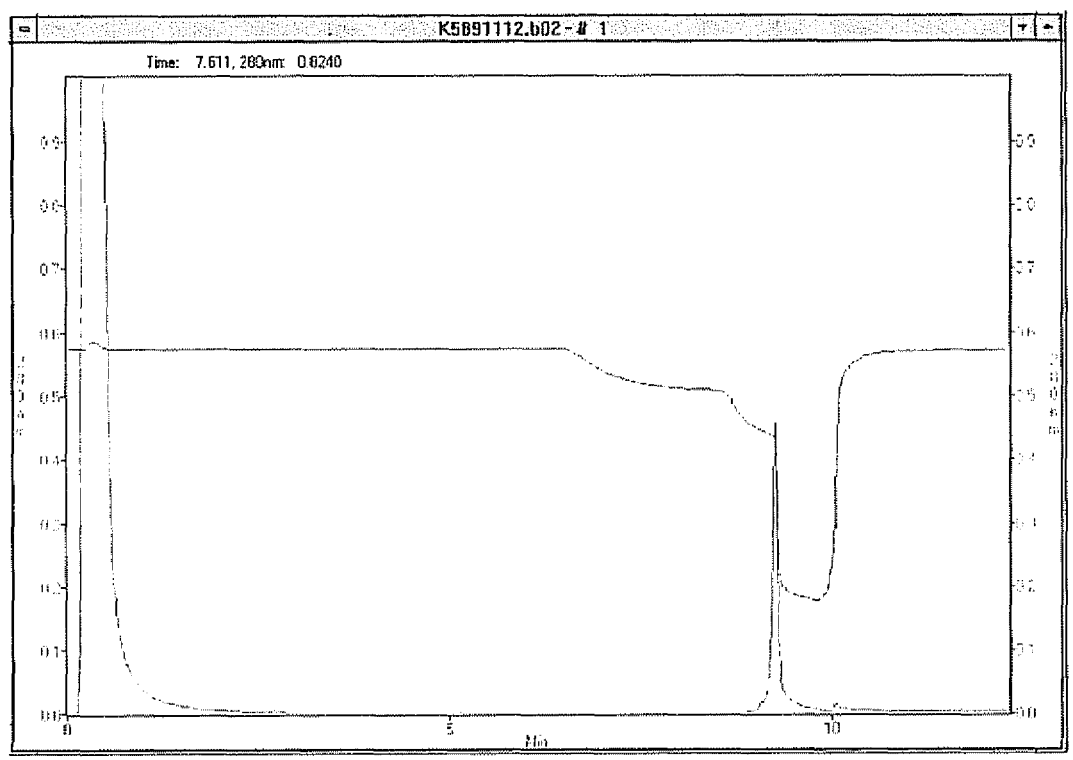
Fig, 13: Result of the affinity chromatography of anti-A-FABP antibodies from goats from a column with bound A-FABP.

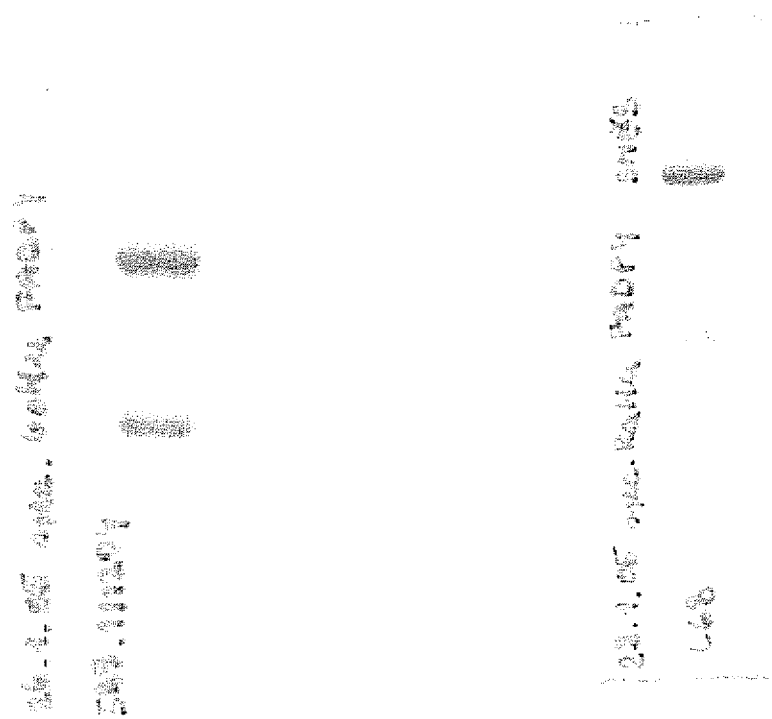
Fig. 14. The cleaned antibodies were separated in 12% SDS-PAGE and dyed with Coomassie Blue (left - goat, right - rabbit).

Fig.: 15. Implementation of an ELISA to determine the concentration of F-ABP from bodily fluid.
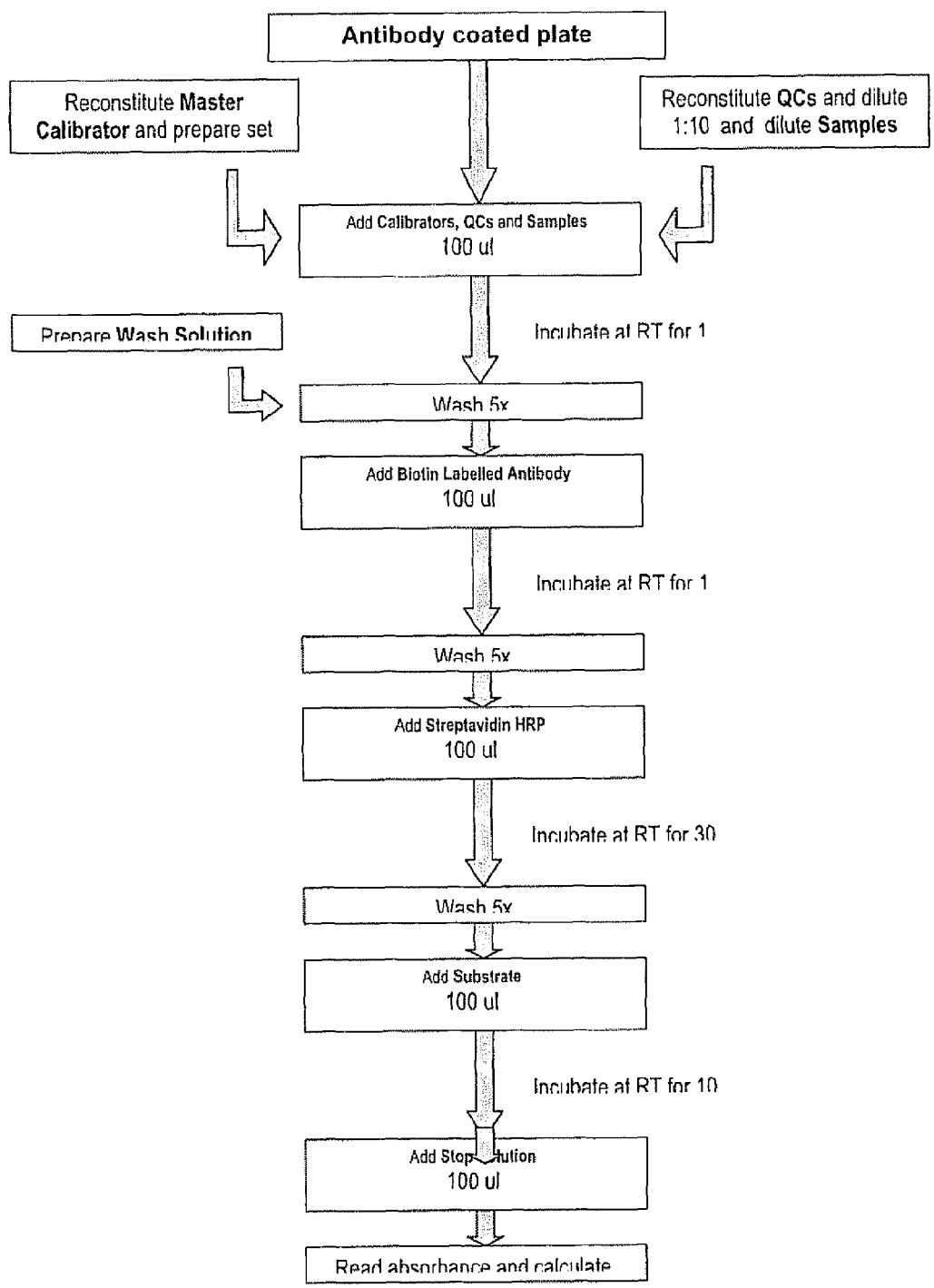

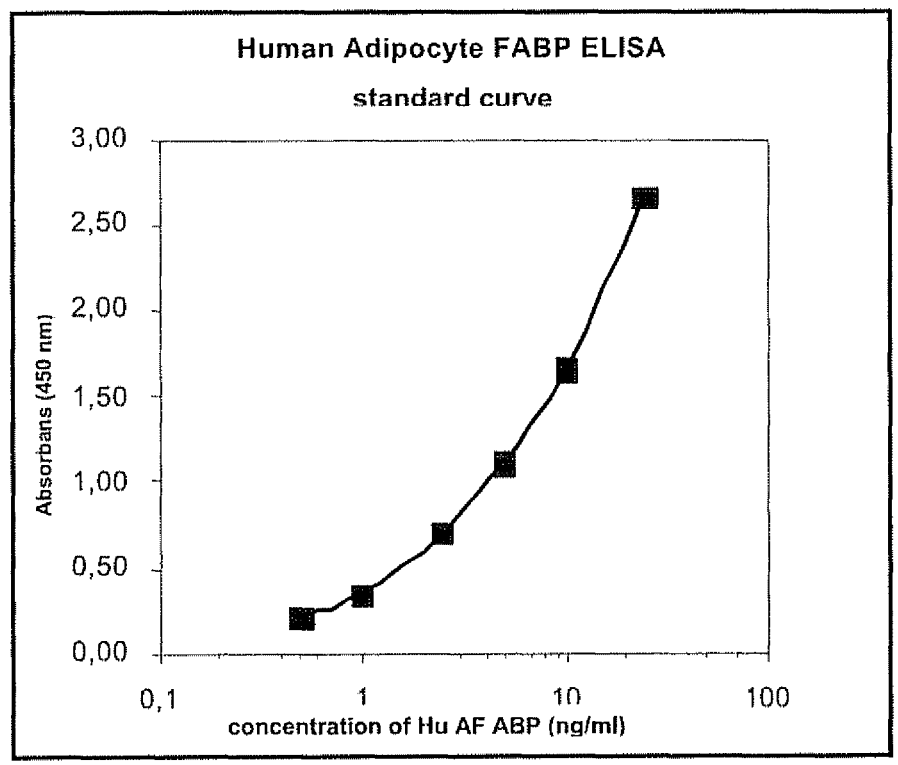
Fig. 16: Typical calibration curve:

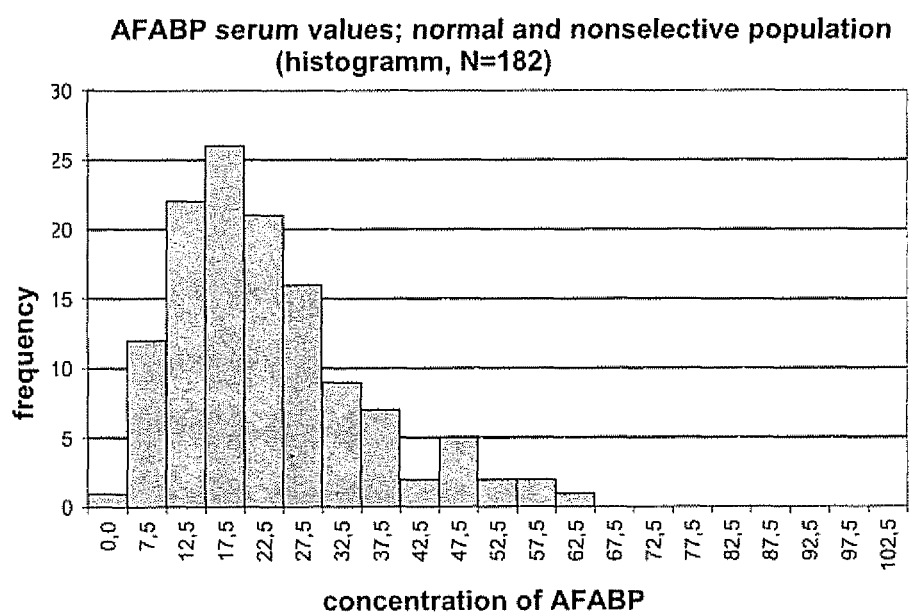
Fig. 17: Distribution of values for AFABP in serum.

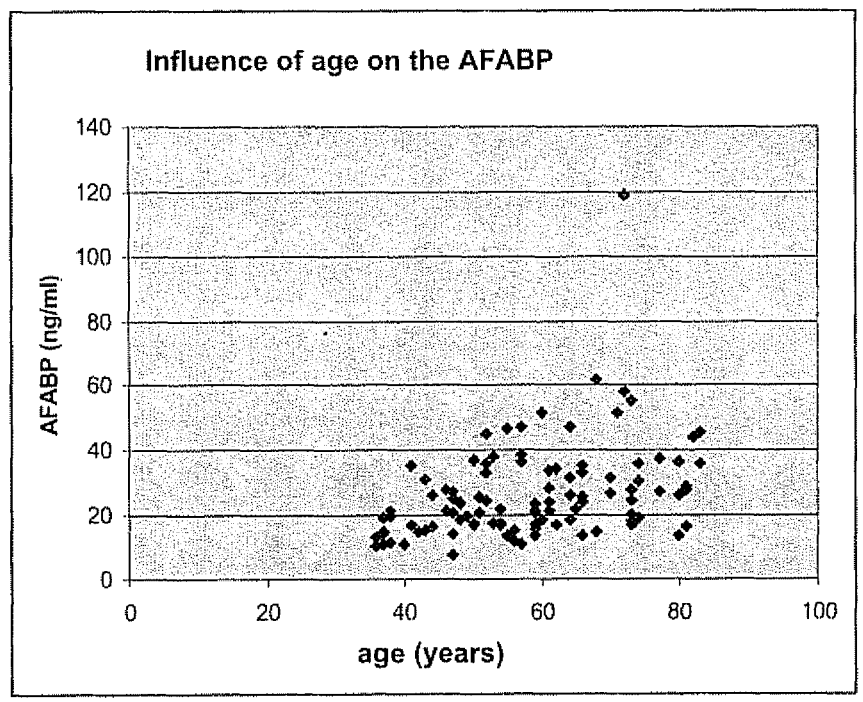
Fig. 18: Influence of age on the AFABP values.

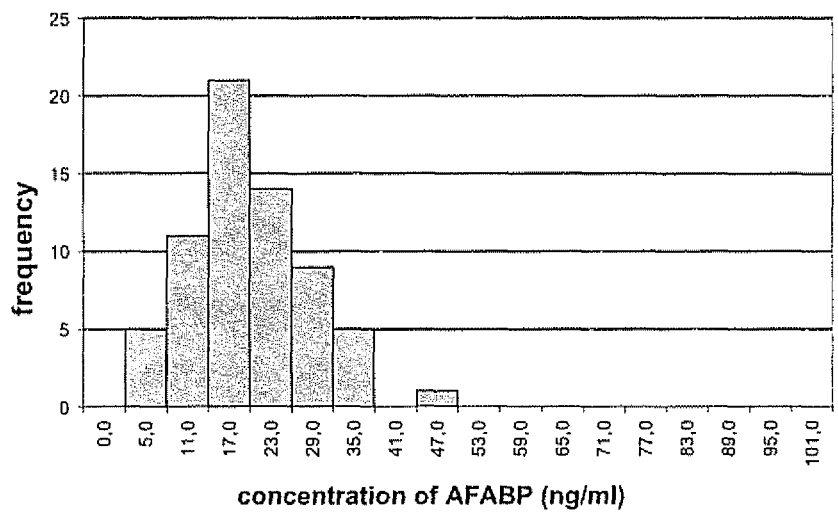
Fig. 19: Establishment of the standard range for A-FABP values in a group of 66 women.

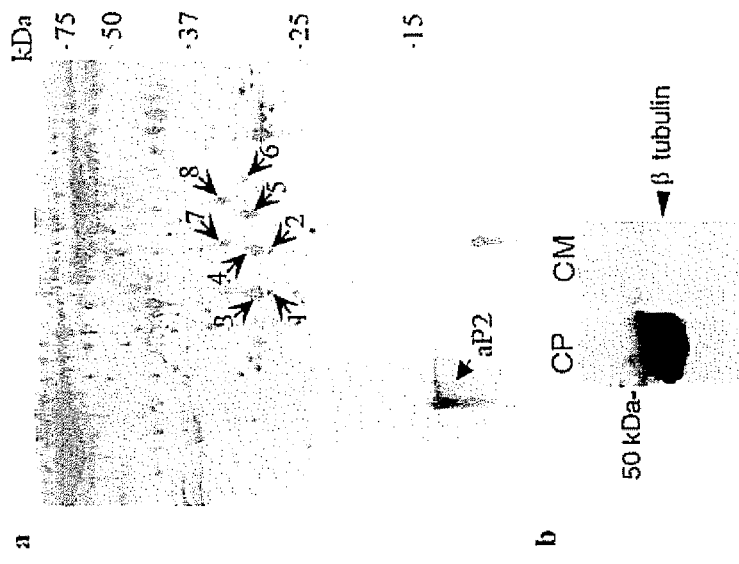
Fig. 20 A-FABP is released into the culture media of adipocytes. Conditioned medium of adipocytes were separated by two dimensional gel electrophoresis. Note that the identity of aP2 was confirmed by Edman degradation sequencing. CM: cell medium; CP: Cell pellet.

Circulating levels of A-FABP in non-obese (BMI<25) and obese (BMI>25) individuals

| | Number (F/M) | Age (yrs) | Serum AFABP (ng/ml) |
|---|---|---|---|
| Obese | 129 (62/67) | 53.9±12.7 | 32.3±14.8** |
| Non-obese | 100 (46/54) | 57.6±12.8 | 20.0±9.8 |

Fig.: 23

METHOD FOR DETERMINING THE CONCENTRATION OF THE ADIPOCYTIC FORM OF THE FATTY ACID BINDING PROTEIN (A-FABP, FABP4, P2)

CROSS-REFERENCE TO RELATED APPLICATIONS

This application is the United States National Phase under 35 U.S.C. §371 of PCT International Application No. PCT/IB2006/002383, filed on Jul. 21, 2006, and claiming priority to German national application no. 10 2005 034 788.6, filed on Jul. 21, 2005.

BACKGROUND OF THE INVENTION

1. Field of the Invention

The invention relates to a method for determining the concentration of the adipocytic form of the fatty acid binding protein (A-FABP, FABP4, P2) for diagnostics and research of the metabolic syndrome, of non-insulin-dependent diabetes (type II diabetes), insulin resistance, obesity (obesitas/adipositas/fatness) and related disorders of the metabolism. It further relates to a test kit for implementation of this method.

Areas of application are medicine and, in particular, medicinal diagnostics.

2. Background of the Related Art

Metabolic syndrome, also known as Syndrome X, insulin resistance syndrome or multiple metabolic syndrome, represents a disorder of metabolism of lipids, carbohydrates, proteins, minerals etc. of the organism, which can be caused by hereditary factors and/or conditions of life. The metabolic syndrome includes: insulin resistance, dyslipidaemia, arterial hypertonia and adipositas.

Insulin resistance is defined as an insensitivity against the body's own insulin. Not only the patients with type II diabetes, but also about 20% of the practically healthy patients who are not overweight suffer from insulin resistance. The causes of insulin resistance have not yet been unambiguously clarified. The characteristics of insulin resistance also include exhaustion of beta cells, their desensitisation and apoptosis caused by hyperinsulinaemia with gluco- and lipotoxicity.

Dyslipidaemia is a disorder of the fat metabolism in form of hypercholesteraemia, hypertriglyceridaemia, hyperlipidaemia (increased blood fat values as a generic term). The latter is characterised by high triglyceride and low HDL cholesterol values, small, dense LDL particles and a high content of free fatty acids. The spectrum of affects ranges from "customary" (polygenic) hypercholerstinaemia (about 10% of the population) to rare, genetically induced lipid metabolism disorders. Dyslipidaemias are risk factors for atherosclerosis, in particular for coronary heart disease. Over and above this, the free fatty acids contribute to maintaining the state of insulin resistance.

Cardiovascular diseases and in particular coronary heart disease (CHD) are the essential complications of metabolic syndrome as regards prognosis and thus the main cause of death for this group of patients.

BRIEF SUMMARY OF THE INVENTION

The objective of the invention is early recognition and/or monitoring of the metabolic syndrome, of type II diabetes, insulin resistance, obesity and/or related disorders of the metabolism. The invention is based on the task of developing methods and test kits with which it is possible to determine suitable parameters for risk assessment and monitoring of the course in diagnosis and therapy of metabolic syndrome, type I diabetes, insulin resistance, obesity I and/or related disorders of the metabolism.

The invention is based on the central idea that the concentration of A-FABP in serum, plasma, urine or other extra-cellular bodily fluids or in the fatty tissue is determined and used for diagnosis or research of the metabolic syndrome, its concomitant diseases, early forms and secondary diseases connected with a disturbance of the fat metabolism.

A very central role in the origination, development and course of the metabolic syndrome and type II diabetes is played by the fat cells and fat metabolism. A cytoplasmatic protein of the fat cells is the adipocytic form of the fatty acid binding protein (abbreviated to A-FABP, FABP4 or P2), which transports longer fatty acids, prostanoids, retinoic acid and similar, non-water-soluble molecules in the cytoplasma of the fat cells. The concentration of A-FABP was compared in the serum of healthy persons and type II diabetics, the body mass index being taken into account as an indication for the share of fatty tissue in the body mass of the persons examined. Although A-FABP is an intra-cellular protein of the fat cells, which hardly ought to appear in the circulation, A-FABP levels in the nanogram range (ng/ml) are found in the serum of normally healthy persons.

As the A-FABP levels in the serum are about twice as high as those of the adipocytic hormone leptin (leptin concentrations±8 ng/ml; A-FABP is ±16-20 ng/ml), it is obvious that A-FABP is actively secreted into the circulation. Further, it cannot be ruled out that a further (signal) effect independent of its intra-cellular function can be ascribed to A-FABP. However, the establishment that measurement of the concentration of A-FABP in bodily fluids is suitable for establishment and monitoring of the metabolic syndrome was completely unexpected.

Thus, the invention is based on the completely surprising knowledge that a significantly increased content of F-ABP in extra-cellular bodily fluids is connected with the metabolic syndrome, its early forms, concomitant diseases and secondary diseases, non-insulin-dependent diabetes (type II diabetes), insulin resistance, obesity (obesitas/adipositas/fatness) and related disorders of the metabolism.

BRIEF DESCRIPTION OF THE FIGURES

FIG. 1: Determination of A-FABP in the serum of 486 volunteers (100 standard-weight, healthy volunteers, 100 patients with dyslipidaemia without obesity and without further features of the metabolic syndrome, 86 type II diabetics, 100 obese and 100 patients with metabolic syndrome.

In the groups of volunteers in question, the A-FABP concentration ranges shown were found (values on the Y axis are ng/ml).

FIG. 2: Correction of the values from FIG. 1 to the Body Mass Index (A-FABP divided by BMI=A_BMI) resulted in the distributions as shown.

FIG. 3: A-FABP values divided by the values of the QUICKI Index

FIG. 4: Correlation between measured concentrations of A-FABP and insulin of volunteers.

FIG. 5: Correlation between measured concentrations of A-FABP and glucose of volunteers.

FIG. 6: Correlation between measured concentrations of A-FABP and QUICKI Index.

FIG. 7: Correlation between measured concentrations of A-FABP and triglycerides

FIG. 8: Correlation of the concentration of A-FABP and E-FABP with total cholesterol from serum (examination of samples from 48 women).

FIG. 9: Correlation of the concentration of A-FABP and E-FABP with HDL cholesterol from serum (examination of samples from 48 women).

FIG. 10: Correlation of the concentration of A-FABP and E-FABP with LDL cholesterol from serum (examination of samples from 48 women).

FIG. 11: Electrophoretic separation by SDS PAGE of cell lysates and visualisation of the protein bands received by Coomassie dyeing.

Description of the tracks
1. $T_0$, i.e. at the moment of addition of IPTG
2. $T_2$, i.e. 2 hours after addition of IPTG
3. $T_4$, i.e. after 4 hours at the end of the expression
4. Supernatant after ultrasound treatment of the bacteria
5. Inclusion corpuscles FIG. 12: Result of the affinity chromatography of anti-A-FABP antibodies from rabbits from a column with bound A-FABP.

FIG. 13: Result of the affinity chromatography of anti-A-FABP antibodies from goats from a column with bound A-FABP.

FIG. 14: The cleaned antibodies were separated in 12% SDS-PAGE and dyed with Coomassie Blue (left—goat, right—rabbit).

FIG. 15: Implementation of an ELISA to determine the concentration of F-ABP from bodily fluid.

FIG. 16: Typical calibration curve.

FIG. 17: Distribution of values for A-FABP in serum.

FIG. 18: Influence of age on the A-FABP values.

FIG. 19: Establishment of the standard range for A-FABP values in a group of 66 women.

FIG. 20: Two-dimensional electrophoresis of the cell culture supernatant of an adipocytic culture.

FIG. 21: Circulating levels of A-FABP in non-obese (BMI<25) and obese (BMI>25) individuals.

Figure 22:
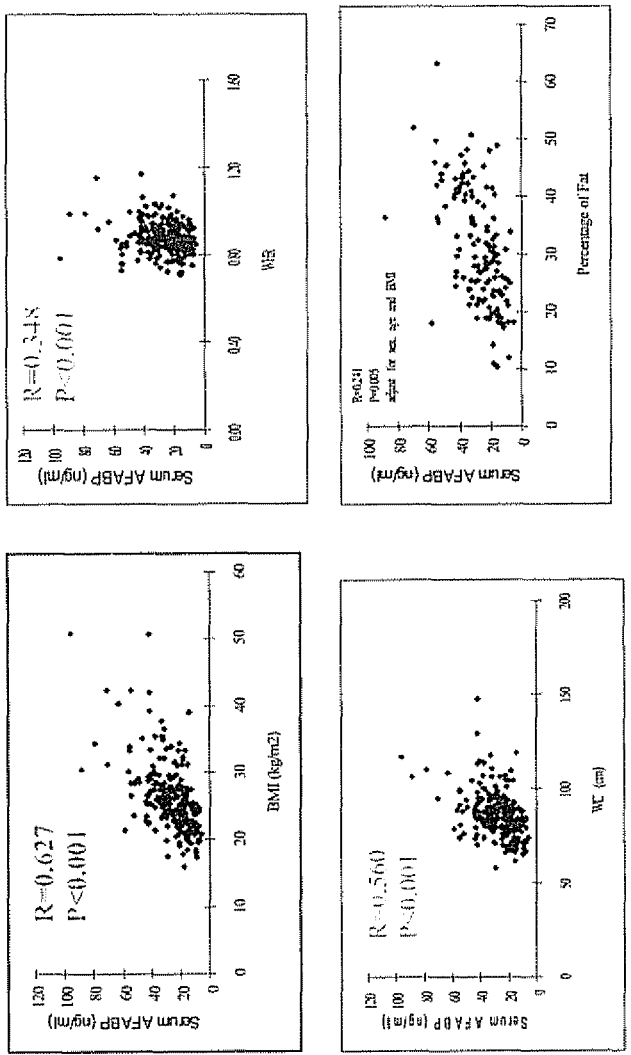

FIG. 22: Serum levels of A-FABP positively correlated with various indexes of obesity (BMI, WHR, WC and fat percentage)

Figure 23:
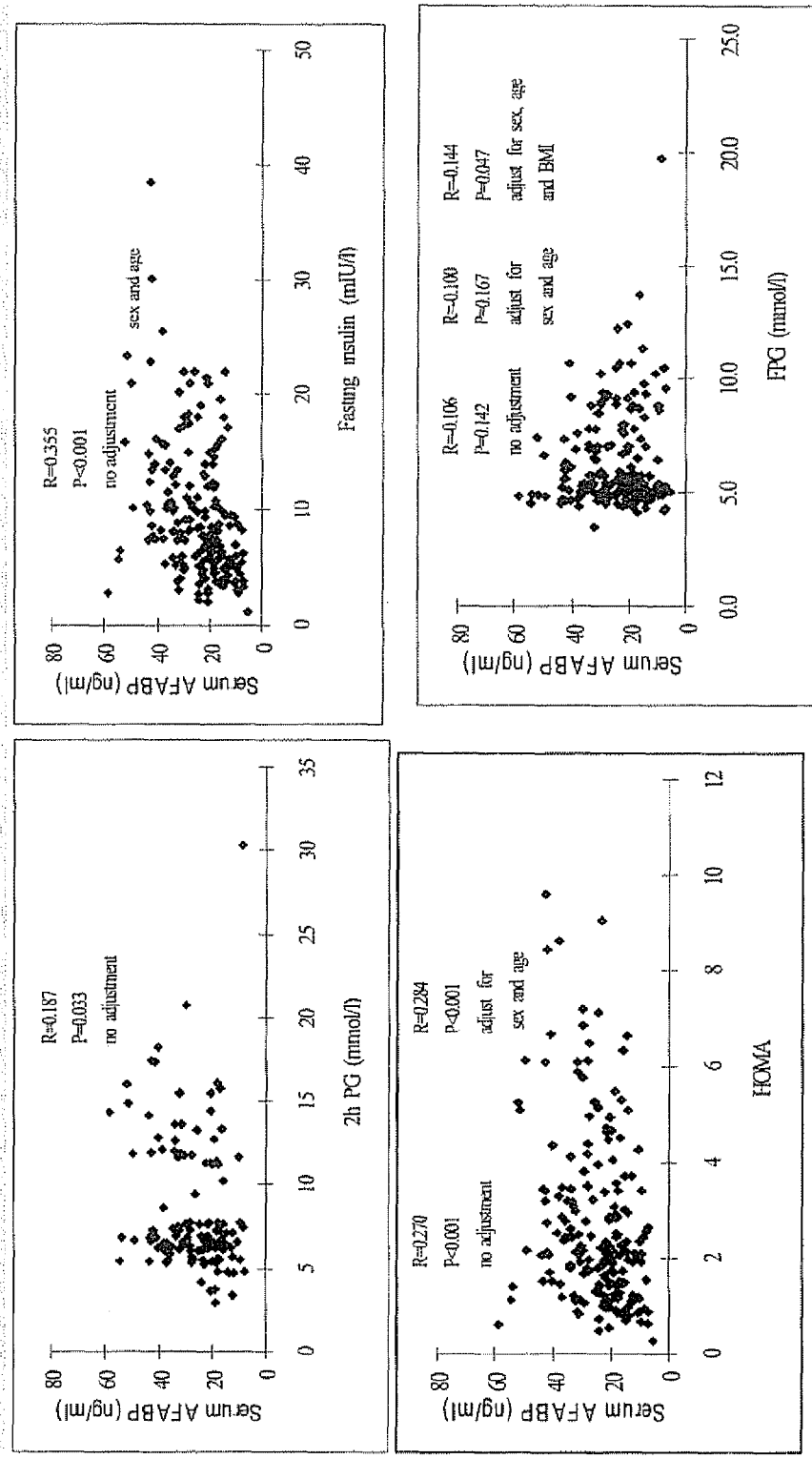
Figure 24:
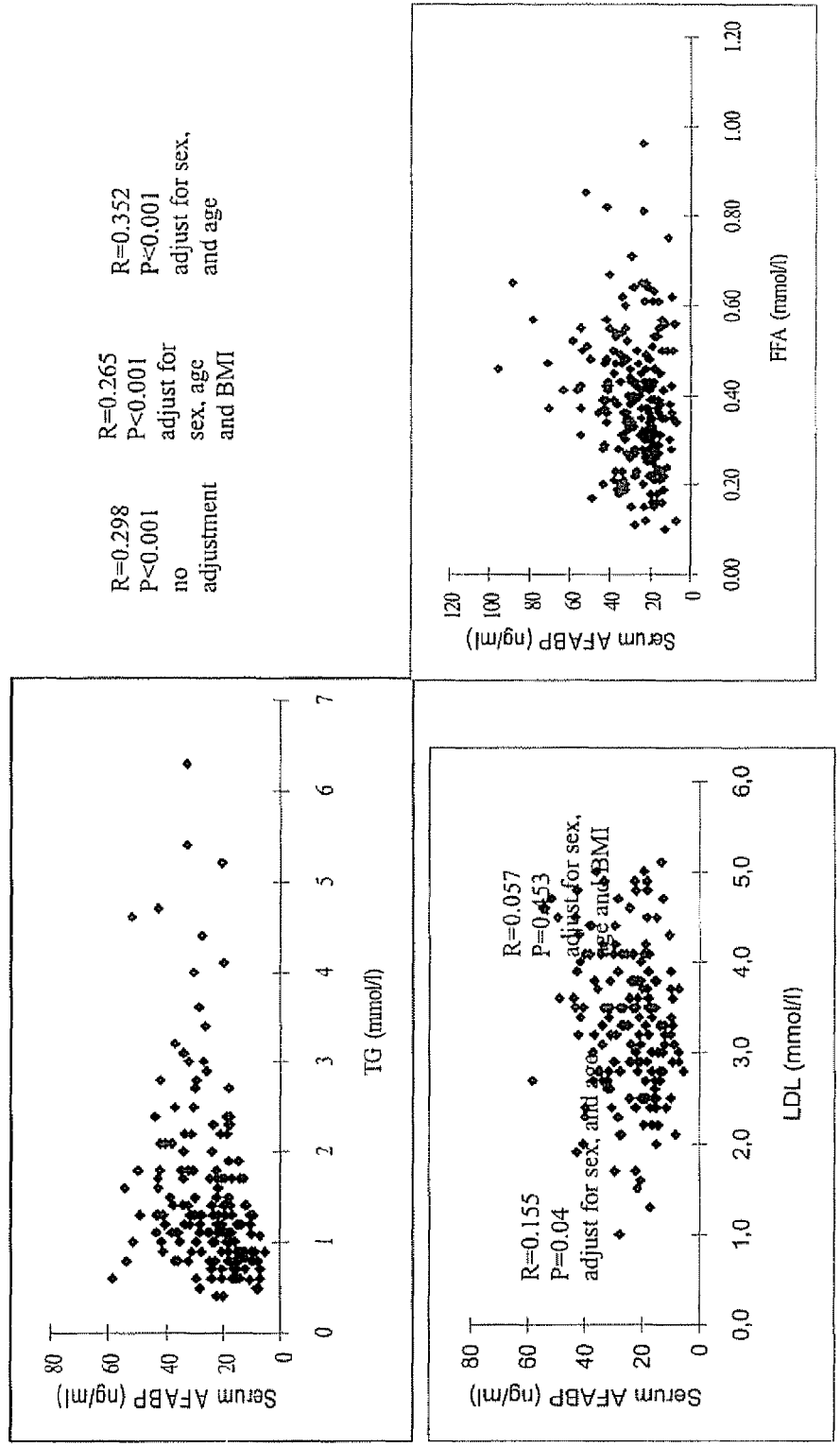
Figure 25:
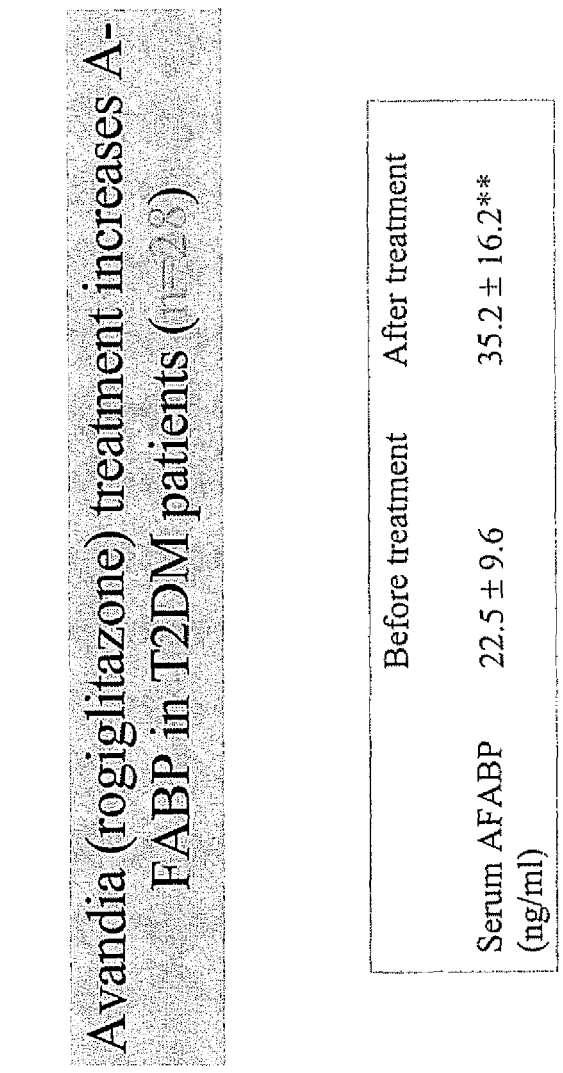

FIG. 23: Correlations of serum A-FABP with insulin sensitivity (HOMA), Fasting insulin, fasting and 2h FP glucose FIG. 24: Positive correlation of A-FABP with LDL, TG and FFA FIG. 25: Avandia® (rogiclitazone) treatment increases A-FABP in T2DM patients (n=28)

DETAILED DESCRIPTION OF THE INVENTION

The invention relates to a method in which the concentration of the F-ABP in bodily fluids, in particular from serum (fatty acid transport capacity), is made use of for diagnosis and/or research of the metabolic syndrome and related metabolic diseases. What was also completely unexpected was the establishment that the concentration of A-FABP in bodily fluids, in particular serum, significantly correlates with the concentration of other parameters of metabolic syndrome, type II diabetes, insulin resistance, obesity and related disorders of the metabolism. For diagnosis and monitoring of the metabolic syndrome and the aforementioned disorders of the metabolism, the concentration of F-ABP in bodily fluids and/or diluted solutions of them is determined.

For the implementation of the invention, immunometric systems, in particular in combination with an optical and/or biosensory evaluation, are particularly suited, as they allow a simple determination of concentration of A-FABP in or from bodily fluids. In this context, various systems, with the help of which the concentration of A-FABP can be determined, for example by parallel or subsequent measurement of various concentrations of the bodily fluid to be determined, can be used, especially if a normalisation/calibration with defined or known A-FABP concentrations is done alongside this, by titration or by the use of various defined concentration of capture molecules, which are bound to a solid phase/carrier material and have affinity to A-FABP or structures derived therefrom.

In this context, methods which entail carrier materials on the surface of which substances suited for determination of the concentration of A-FABP in or from bodily fluids have been immobilised are favourable. These can in particular be molecules or substances composed thereof, preferably proteins, which have an affinity to F-ABP, for example anti-F-ABP-antibodies. What is also possible is the use of immobilised substances which have affinity to part fragments of A-FABP, in particular peptide chains, or peptides composed of part fragments.

As a carrier material, all possible materials or coated materials on the surfaces of which molecules can be immobilised are suited, in particular nitrocellulose or PVDF or other materials for bio-physical immobilisation, e.g. in wells of ELISA plates. But an immobilisation via electrostatic interaction or immobilisation by chemical compounding, for example by use of so-called (cross-)linkers, is also possible. For example, gold or coated gold surfaces are also suited for immobilisation, in particular for biosensory measurements, for example of surface plasmon resonance or electrochemical variables. A benefit for the implementation of the method according to the invention is in particular carrier materials with surfaces which have at least a partly planar surface, for example glass or plastic chips or ELISA plates, as they permit a particularly simple implementation of the method according to the invention, for example with the help of scanners or ELISA readers. Alongside planar surfaces, on which locally addressed areas, for example spots, have been formed with immobilised capture molecules, in particular with anti-FABP antibodies, for example on surfaces of cellulose or chips, the base surfaces of the wells of ELISA plates are in particular suited for the determination of the A-FBP concentration from bodily fluids.

As an immunometric system, the so-called Enzyme Linked Immunosorbent Assay (ELISA) or comparable systems using dye-marked molecules are particularly sensible, as a result of which a particularly high sensitivity of the system for determination of the A-FABP concentration is achieved. In this context, a carrier material on which one or more substance(s), e.g. antibodies, with affinity to A-FABP or derived molecules has/have been immobilised is put into contact with bodily fluid or solutions containing bodily fluid, with the result that the A-FABP or the derived form/course, if applicable in the solution with bodily fluid, can associate with the substances in the vicinity of the surface of the carrier material. For this purpose, the bodily fluid can have been dissolved in an incubation solution, e.g. blocking buffer, which leads, for example, to an improvement of the signal/sound ratio as a result of reduction of unspecific interactions. As proof of the associated A-FABP or derived molecules on the surface, a dissolved substance, preferably anti-A-FABP antibodies, is put onto the carrier material, mainly following a washing step, in which context the dissolved detection substance likewise has affinity to A-FABP and binds to the associated A-FABP in the vicinity of the carrier material.

The detection substance/antibodies bound on the A-FABP or the molecules derived therefrom can be detected in various ways. It is possible that the detection substance or anti-A-

FABP antibodies has/have already been provided with a marking, for example with a dye, in particular fluorescent dye, or with an enzyme which can convert a substrate, for example from a detection solution, with optical detection, e.g. horseradish peroxidase or alkaline phosphatase. The detection substance, in particular antibodies, can however also have been provided with a molecule, e.g. biotin, which for its part also has affinity to another marked substance, e.g. streptavidin. If the detection substance/anti-A-FABP antibody itself has not been marked, marked secondary antibodies are in particular suited, these being added, mainly after a washing step, and making the detection substance/anti-A-FABP antibody visible on the surface of the carrier material or making the subsequent optical evaluation possible.

For the diagnosis and research of metabolic syndrome, its early forms, concomitant and secondary diseases, type II diabetes, insulin resistance, obesity or related disorders of the metabolism, a further benefit which is suitable is the fact that the A-FABP concentration measured in accordance with the invention is placed in a reference with other characteristics, e.g. age or gender, the body mass index or with components of the metabolism which are characteristic for the metabolic syndrome, in particular insulin (for example Quicki values), glucose, triglyceride, adiponectin, leptin, total cholesterol, HDL cholesterol and/or LDL cholesterol. As a result of the combination of A-FABP with at least one further parameter, a prognosis of other parameters of the metabolic syndrome is also beneficially possible.

As a result of the implementation of the invention, a deduction to characteristics of the metabolic syndrome is possible in a very simple way, also enabling a particularly simple and favourably priced diagnosis or monitoring of the metabolic syndrome, of type II diabetes, insulin resistance, obesity (obesitas/adipositas/fatness) and related disorders of the metabolism. For example, no removal of tissue samples is necessary, as deduction directly to the pathogenic processes in the tissue or in the cells, as the case may be, is possible. A further particular benefit of the invention is the fact that early stages of the metabolic syndrome are detectable. In this way, it becomes possible, for the first time, to initiate countermeasures for patients before the occurrence of the pathogenic phenomena connected with the metabolic syndrome, for example by prescription of a diet or sport or by administration of a suitable medication.

As a result of the invention, the use of A-FABP as a substance similar to a hormone for influencing the fat, sugar and energy metabolism is made possible (cf. FIG. 20). If a positive effect of A-FABP is seen, it or its fragments or its mimetics are applicable as medication. If the effect is negative, A-FABP blockers are of medicinal benefit.

FIG. 20 shows a two-dimensional electrophoresis of the cell culture supernatant of an adipocytic culture, in which a very large and distinct spot of the A-FABP can be seen (the identity of the protein is determined by means of N-terminal sequencing with a mass spectrometer). The fact that no beta-tubulin (an intra-cellular structure protein) could be detected in the supernatant with the Western Blot is an indication for the fact that the A-FABP does NOT enter the medium by the decay of the fat cells, but really by secretion.

Thus, the invention provides a completely new possibility of risk assessment and course monitoring in the diagnostics and therapy of metabolic syndrome and type II diabetes.

The invention is to be explained in more detail below with the help of examples of application:

Embodiment 1

In 486 volunteers, A-FABP in the serum was determined. These were 100 healthy volunteers of standard weight, 100 patients with dyslipidaemia without obesity and without other features of metabolic syndrome, 86 type II diabetics, 100 obese and 100 patients with metabolic syndrome. Alongside A-FABP, the following parameters were also determined: body mass index (BMI), glucose, insulin, quantitative insulin sensitivity check index (QUICKI), adiponectin and E-FABP (epidermal fatty acid binding protein).

In the individual groups of volunteers, A-FABP concentration ranges were found as portrayed in FIG. 1.

A correction to the body mass index (A-FABP divided by BMI) resulted in distributions according to FIG. 2.

After the division of the A-FABP values by the values of the QUICKI index, the distribution shown in FIG. 3 resulted.

From the measured data, it was seen as a complete surprise and unambiguously that the A-FABP levels discriminate very effectively between healthy standard volunteers and patients with metabolic syndrome, this being independent of the body mass index.

In addition, the concentrations of glucose, insulin, quantitative insulin sensitivity check index (QUICKI) and triglycerides were measured and placed into correlation with the measured values of A-FABP (FIGS. 4-7).

It was clearly recognisable that the measured values of glucose, insulin, QUICKI and triglycerides, i.e. characterising parameters for the metabolic syndrome, are in a direct correlation with the concentration of the measured A-FABP.

If the values from FIG. 1 and FIG. 2 are additionally used, it becomes clear that the measured values of the A-FABP from bodily fluids are in a direct connection with the metabolic syndrome and the related metabolic diseases.

Embodiment 2

On 48 women whose serum samples were available, amongst whom there could also be women with metabolic syndrome, the concentrations of A-FABP, E-FABP, total cholesterol, HDL cholesterol and LDL cholesterol were determined. Application of the values of A-FABP and E-FABP against each of the values of total cholesterol (FIG. 8), HDL cholesterol (FIG. 9) and LDL cholesterol (FIG. 10) clearly showed that A-FABP closely correlates with the most important parameters of the metabolic syndrome, of type II diabetes, insulin resistance, obesity (obesitas/adipositas/fatness) and related disorders of the metabolism.

Embodiment 3

Production of the Recombinant Human A-FABP cDNA Sequence:

(SEQ ID NO: 1)
ATGTGCGATGCGTTTGTGGGCACCTGGAAACTGGTTAGCAGCGAAAACTT

CGATGATTACATGAAAGAAGTGGGCGTTGGTTTTGCGACCCGCAAAGTTG

CGGGTATGGCGAAACCGAACATGATTATCAGCGTGAACGGCGATGTGATT

ACCATCAAAAGCGAAAGCACCTTCAAAAACACCGAAATCAGCTTTATCCT

GGGCCAGGAATTTGATGAAGTGACCGCGGATGATCGTAAAGTGAAAAGCA

CCATCACCCTGGATGGTGGTGTTCTGGTGCATGTGCAGAAATGGGATGGC

AAAAGCACCACCATCAAACGCAAACGCGAAGATGATAAACTGGTGGTGGA

ATGCGTGATGAAAGGTGTTACCAGCACCCGTGTTTATGAACGTGCG

Amino Acid Sequence:

(SEQ ID NO: 2)
MCDAFVGTWKLVSSENFDDYMKEVGVGFATRKVAGMAKPNMIISVNGDVI

TIKSESTFKNTEISFILGQEFDEVTADDRKVKSTITLDGGVLVHVQKWDG

KSTTIKRKREDDKLVVECVNKGVTSTRVYERA

The expressed protein contained no additional amino acids or tags.
Protein Size:
  132 amino acids; molar mass: approx. 14,720 Da
Expression Stem:
  E. coli: BL21 DE3(pRSET-FABP4)-1
Expression Method:
  SOB-Medium (4.5 l) was inoculated with an overnight culture of E. coli BL21 DE3(pRSET-FABP4)-1.
  Cultivation was on a shaker at 37° C.
  Inductor IPTG was added after 3.5 hours of the cultivation at OD=0.69.
  The expression was ended after 4 hours. The optical density reached OD=1.52.
  The bacteria were centrifuged off and concentrated to a theoretical OD=100 in 68.4 ml PBS buffer.
  Soluble A-FABP was obtained by ultrasound treatment of the bacteria.
Expression Analysis of A-FABP (FIG. 11).
  As the result of the protein separation, A-FABP was detectable within tracks 2-5 as distinct protein bands, whereas control track 1 did not show any corresponding bands.
Obtaining Antibodies and Processing
  Against A-FABP, polyclonal antibodies were produced and affinity-cleaned.
1. Immunisation of the Animals
1.1 Goat
  Goat no. 589 was immunised according to the following scheme:

| | | |
|---|---|---|
| $1^{st}$ day | 8x intradermal | 1000 μg antigen + CFA, 1:1 |
| $21^{st}$ day | 2x subcutaneous | 1000 μg antigen + ICFA, 1:1 |
| $28^{th}$ day | 2x subcutaneous | 500 μg antigen + ICFA, 1:1 |
| $35^{th}$ day | 2x subcutaneous | 500 μg antigen + ICFA, 1:1 |
| $45^{th}$ day | blood taken | 160 ml of blood |
| $105^{th}$ day | 2x subcutaneous | 500 μg antigen + ICFA, 1:1 |
| $112^{th}$ day | 2x subcutaneous | 500 μg antigen + ICFA, 1:1 |
| $122^{nd}$ day | blood taken | 200 ml of blood |
| $182^{nd}$ day | 2x subcutaneous | 500 μg antigen + ICFA, 1:1 |
| $189^{th}$ day | 2x subcutaneous | 500 μg antigen + ICFA, 1:1 |
| $199^{th}$ day | blood taken | 200 ml of blood |

CFA—complete Freund adjuvant
IFCA—incomplete Freund adjuvant 1.2 Rabbits
  Rabbits no. 68 and 69 were immunised according to the following scheme:

| | | |
|---|---|---|
| $1^{st}$ day | 8x intradermal | 200 μg antigen + CFA, 1:1 |
| $21^{st}$ day | 2x subcutaneous | 200 μg antigen + ICFA, 1:1 |
| $28^{th}$ day | 2x subcutaneous | 100 μg antigen + ICFA, 1:1 |
| $35^{th}$ day | 2x subcutaneous | 100 μg antigen + ICFA, 1:1 |
| $45^{th}$ day | blood taken | 50 ml of blood |
| $105^{th}$ day | 2x subcutaneous | 100 μg antigen + ICFA, 1:1 |
| $112^{th}$ day | 2x subcutaneous | 100 μg antigen + ICFA, 1:1 |
| $122^{nd}$ day | blood taken | 50 ml of blood |
| $182^{nd}$ day | 2x subcutaneous | 100 μg antigen + ICFA, 1:1 |
| $189^{th}$ day | 2x subcutaneous | 100 μg antigen + ICFA, 1:1 |
| $199^{th}$ day | blood taken | 50 ml of blood |

CFA—complete Freund adjuvant
IFCA—incomplete Freund adjuvant

2. Obtaining of Serum
  Blood (from both goat and also rabbit) was centrifuged for 20 minutes at 4° C. and at 2,400 G, the serum obtained stored at −20° C.
3. Affinity Cleaning
3.1 Production of the Affinity Column
  Poros AL (Applied Biosystems), 0.45 g, was provided with 1 mg of A-FABP in accordance with the manufacturer's instructions.
3.2 Antibody Cleaning
  Antibodies were bound to the column in 0.1M PBS, pH 7.4 and eluted with 0.1 PBS, 13 mM HCl, 0.15 mM NaCl.
  The results of the affinity chromatograms can be seen in FIG. 12 (cleaning of antibodies from rabbits) and in FIG. 13 (cleaning of antibodies from goats).
3.3 Testing the Antibodies for Purity and Titre Determination
3.3.1 The cleaned antibodies were separated in 12% SDS-PAGE and dyed with Coomassie Blue (FIG. 14).
3.3.2 Titre determination with indirect ELISA
  A microtitre plate (Nunc) was coated with 25 mg/well A-FABP.
  Affinity-cleaned antibodies were pipetted in an initial concentration of 1 mg/ml and diluted 1:3 in series.
  Titre was defined as an antibody dilution which has an absorbance of less than 1.5:
Goat:
  Titre: 270,000.-, quantity 4.4 mg
Rabbit
  Titre: larger than 90,000, quantity: 4.8 mg
ELISA Development:
ELISA Plate:
  For coating of the microtitre plate, the affinity-cleaned goat antibody (4 μg/ml) was used in hydrogen carbonate buffer (0.1 M). After an overnight coating at 4.0° C., the plates were washed with PBS and blocked for 30 minutes at room temperature with 0.5% BSA in TPS, 4% saccharose.
Conjugate:
  Affinity-cleaned rabbit antibody was conjugated with Biotin-LC-LC-NHS-sulfo, Pierce, cat. no. 21338, in accordance with the manufacturer's instructions and used in a concentration of 33 μg/ml.
  Streptavidin-HRP conjugate was purchased from the firm of Roche (catalogue number 1 089 153).
Calibrator:
  Recombinant human A-FABP was lyophilised and used as a master calibrator in an initial concentration of 500 ng/ml.
  The actual ELISA test was held as shown in FIG. 15.
  Finally, the following characteristics of the tests were set:
a) typical calibration curve for human A-FABP: with the ELISA held, a sensitivity of the concentration measurement of A-FABP of less than 100 pg/ml resulted (FIG. 16).
b) Recovery/dilution (see table 1)

TABLE 1

| Sample | Dilution | Monitored (ng/ml) | Expected (ng/ml) | Recovery O/E (%) |
|---|---|---|---|---|
| 1 | — | 36.8 | — | — |
| | 1:2 | 19.6 | 18.4 | 106.5 |

TABLE 1-continued

| Sample | Dilution | Monitored (ng/ml) | Expected (ng/ml) | Recovery O/E (%) |
|---|---|---|---|---|
|  | 1:4 | 9.9 | 9.2 | 107.6 |
|  | 1:8 | 4.9 | 4.6 | 106.5 |
| 2 | — | 28.1 | — | — |
|  | 1:2 | 14.1 | 14.1 | 100.0 |
|  | 1:4 | 7.8 | 7.0 | 111.0 |
|  | 1:8 | 3.9 | 3.5 | 111.0 | c) Recovery/Addition (see Table 2)

TABLE 2

| Sample | Monitored (ng/ml) | Expected (ng/ml) | Recovery O/E (%) |
|---|---|---|---|
| 1 | 8.9 | — | — |
|  | 16.5 | 18.9 | 87.3 |
|  | 24.1 | 28.9 | 83.4 |
|  | 55.5 | 58.9 | 94.2 |
| 2 | 6.8 | — | — |
|  | 15.4 | 16.8 | 91.7 |
|  | 24.2 | 26.8 | 90.3 |
|  | 53.1 | 36.8 | 93150 | d) Precision intra-assay (see Table 3)

TABLE 3

| Sample | Mean (ng/ml) | SD (ng/ml) | CV (%) |
|---|---|---|---|
| 1 | 13.9 | 0.92 | 6.6 |
| 2 | 27.3 | 1.08 | 3.9 | e) Precision intra-assay (see Table 4)

TABLE 4

| Sample | Mean (ng/ml) | SD (ng/ml) | CV (%) |
|---|---|---|---|
| 1 | 12.5 | 0.32 | 2.6 |
| 2 | 31.1 | 1.58 | 5.1 | f) A value distribution for A-FABP for healthy adults as portrayed in FIG. 17 resulted.

g) The influence of age on the A-FABP values was established in accordance with FIG. 18.

h) The influence of gender on the A-FABP values was established (see Table 5).

TABLE 5

| | Age | Total cholesterol mmol/l | HDL-chol. mmol/l | LDL-chol. mmol/l | Triglyceride mmol/l | AFABP ng/ml |
|---|---|---|---|---|---|---|
| Mean (women): | 45.5 | 5.21 | 1.46 | 3.35 | 1.13 | 21.18 |
| Mean (men): | 43.7 | 5.08 | 1.06 | 3.70 | 1.61 | 21.44 | i) In a group of 66 women, the standard area was established or set (see also FIG. 18):
Minimum: 7.7 ng/ml
Maximum: 45.1 ng/ml
Mean: 19.58 ng/ml
Standard deviation: 8.16
Normal range: $(x \pm 2\ s)$: $19.8 \pm 16.32$ ng/ml

---

The invention claimed is:

1. A method for the diagnosis of metabolic syndrome, comprising:
   obtaining a sample of human serum or plasma from a subject suspected of having a metabolic syndrome,
   measuring a concentration of the adipocytic form of a fatty acid binding protein (A-FABP) in said human serum or plasma from said subject suspected of having a metabolic syndrome, including the step of immobilizing the A-FABP on an immobilization medium, wherein the immobilization medium is selected from the group consisting of gold and a gold coated surface, and
   diagnosing metabolic syndrome on the basis of the measured concentration of A-FABP, wherein the diagnosis is positive if said concentration is elevated relative to a baseline level.

2. The method of claim 1, wherein an immunometric system is used for the measuring of the concentration of the A-FABP.

3. The method of claim 2, wherein carrier material on which substances with affinity to A-FABP or parts thereof have been immobilised is used.

4. The method of claim 3, wherein the immobilised substances with affinity to A-FABP or parts thereof are manifested as antibodies.

5. The method of claim 3, wherein the carrier material has at least a partly planar surface.

6. The method of any of claims 3-5, wherein the carrier material is an ELISA plate.

7. The method of any of claims 2-5, wherein the immunometric system is an ELISA.

8. The method of claim 7, wherein the ELISA contains anti-A-FABP antibodies, secondary detection antibodies, carrier materials, washing, incubation and detection solutions.

9. The method of claim 2, wherein the determining step is accomplished through a scanner or ELISA reader.

10. The method of claim 9, wherein the concentration of A-FABP is placed into reference with at least one further characteristic selected from the group consisting of body mass index, insulin, glucose, quantitative insulin sensitivity check index, adiponectin and epidermal fatty acid binding protein.

* * * * *

SEQUENCE LISTING

<160> NUMBER OF SEQ ID NOS: 2

<210> SEQ ID NO 1
<211> LENGTH: 396
<212> TYPE: DNA
<213> ORGANISM: Homo sapiens
<220> FEATURE:
<221> NAME/KEY: misc_feature
<223> OTHER INFORMATION: A-FABP cDNA

<400> SEQUENCE: 1

```
atgtgcgatg cgtttgtggg cacctggaaa ctggttagca gcgaaaactt cgatgattac      60
atgaaagaag tgggcgttgg ttttgcgacc cgcaaagttg cgggtatggc gaaaccgaac     120
atgattatca gcgtgaacgg cgatgtgatt accatcaaaa gcgaaagcac cttcaaaaac     180
accgaaatca gctttatcct gggccaggaa tttgatgaag tgaccgcgga tgatcgtaaa     240
gtgaaaagca ccatcaccct ggatggtggt gttctggtgc atgtgcagaa atgggatggc     300
aaaagcacca ccatcaaacg caaacgcgaa gatgataaac tggtggtgga atgcgtgatg     360
aaaggtgtta ccagcacccg tgtttatgaa cgtgcg                              396
```

```
<210> SEQ ID NO 2
<211> LENGTH: 132
<212> TYPE: PRT
<213> ORGANISM: Homo sapiens
<220> FEATURE:
<221> NAME/KEY: MISC_FEATURE
<223> OTHER INFORMATION: A-FABP Protein

<400> SEQUENCE: 2

Met Cys Asp Ala Phe Val Gly Thr Trp Lys Leu Val Ser Ser Glu Asn
1               5                   10                  15

Phe Asp Asp Tyr Met Lys Glu Val Gly Val Gly Phe Ala Thr Arg Lys
            20                  25                  30

Val Ala Gly Met Ala Lys Pro Asn Met Ile Ile Ser Val Asn Gly Asp
        35                  40                  45

Val Ile Thr Ile Lys Ser Glu Ser Thr Phe Lys Asn Thr Glu Ile Ser
    50                  55                  60

Phe Ile Leu Gly Gln Glu Phe Asp Glu Val Thr Ala Asp Asp Arg Lys
65                  70                  75                  80

Val Lys Ser Thr Ile Thr Leu Asp Gly Gly Val Leu Val His Val Gln
            85                  90                  95

Lys Trp Asp Gly Lys Ser Thr Thr Ile Lys Arg Lys Arg Glu Asp Asp
            100                 105                 110

Lys Leu Val Val Glu Cys Val Met Lys Gly Val Thr Ser Thr Arg Val
            115                 120                 125

Tyr Glu Arg Ala
    130
```